(12) United States Patent
Samson et al.

(10) Patent No.: US 6,383,205 B1
(45) Date of Patent: May 7, 2002

(54) MECHANICAL CLOT TREATMENT DEVICE WITH DISTAL FILTER

(75) Inventors: Gene Samson, Milpitas; Harold F. Carrison, Pleasanton, both of CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

(21) Appl. No.: 09/452,528

(22) Filed: Dec. 1, 1999

Related U.S. Application Data

(63) Continuation of application No. 08/941,514, filed on Sep. 30, 1997, now Pat. No. 6,066,149.

(51) Int. Cl.$^7$ .............................................. A61M 29/00
(52) U.S. Cl. ...................................................... 606/200
(58) Field of Search ............................... 606/200, 159, 606/158, 198; 604/104, 114, 113, 127, 128

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 3,367,101 A | 2/1968 | Garner et al. |
| 3,435,826 A | 4/1969 | Fogarty |
| 3,753,700 A | 8/1973 | Harrison et al. |
| 3,996,938 A | 12/1976 | Clark, III |
| 4,030,503 A | 6/1977 | Clark, III |
| 4,295,464 A | * 10/1981 | Shihata ........................ 128/1 R |
| 4,403,612 A | 9/1983 | Fogarty |
| 4,425,908 A | * 1/1984 | Simon ......................... 128/1 R |
| 4,561,439 A | * 12/1985 | Bishop et al. ............ 128/348.1 |
| 4,643,184 A | 2/1987 | Mobin-Uddin |
| 4,692,139 A | 9/1987 | Stiles |
| 4,706,671 A | 11/1987 | Weinrib |

(List continued on next page.)

FOREIGN PATENT DOCUMENTS

| | | |
|---|---|---|
| CA | 2000621 | 4/1990 |
| EP | 0 117 940 | 9/1984 |
| EP | 0 418 677 | 3/1991 |
| EP | 0 419 154 A1 | 3/1991 |
| EP | 0 472 368 | 2/1992 |
| EP | 0 531 822 | 3/1993 |
| EP | 0 533 511 A1 | 3/1993 |
| EP | 0 737 450 | 10/1996 |
| GB | 2 020 557 | 11/1979 |
| WO | WO 94/24946 | 11/1994 |
| WO | WO 95/35066 | 12/1995 |
| WO | WO 96/01591 | 1/1996 |
| WO | WO 97/42878 | 11/1997 |
| WO | WO 98/02084 | 1/1998 |

OTHER PUBLICATIONS

Castañeda–Zuñiga, W.R., ed., (1997). *Interventional Radiology*. vol. 1, Third Edition, Williams & Wilkins: New York, pp. 912–921.

*Primary Examiner*—Eduardo C. Robert
(74) *Attorney, Agent, or Firm*—Lyon & Lyon

(57) ABSTRACT

A surgical device for opening a passageway adjacent a thrombus to allow both blood and medication to bypass a clot. The surgical device may also be used to pierce and remove a thrombus. The device includes a core element or wire having an expanding proximal cage assembly and a distal filter or expanding cage assembly placed around the core wire. Components of the device are preferably radio-opaque. The proximal end of the proximal cage may be affixed to an actuator to allow expansion of the cage after deployment. The proximal cage assembly may be used for collecting emboli or for displacing emboli to allow blood flow to resume, either with or without concurrent clot-dissolving drug treatment. The distal section is placed distally of the thrombus to collect portions of the thrombus which may loosen during the treatment or removal procedure.

21 Claims, 6 Drawing Sheets

U.S. PATENT DOCUMENTS

| | | |
|---|---|---|
| 4,762,130 A | 8/1988 | Fogarty et al. |
| 4,790,812 A | 12/1988 | Hawkins, Jr. et al. |
| 4,842,579 A | 6/1989 | Shiber |
| 4,873,978 A | 10/1989 | Ginsburg |
| 4,885,003 A | 12/1989 | Hillstead |
| 4,890,611 A | 1/1990 | Monfort et al. |
| 4,904,431 A | 2/1990 | O'Maleki |
| 4,921,484 A | 5/1990 | Hillstead |
| 4,926,858 A | 5/1990 | Gifford, III et al. |
| 4,997,435 A | 3/1991 | Demeter |
| 5,002,560 A * | 3/1991 | Machold et al. ............ 606/198 |
| 5,011,488 A | 4/1991 | Ginsburg |
| 5,053,008 A | 10/1991 | Bajaj |
| 5,100,423 A | 3/1992 | Fearnot |
| 5,112,347 A | 5/1992 | Taheri |
| 5,122,136 A | 6/1992 | Guglielmi et al. |
| 5,133,733 A * | 7/1992 | Rasmussen et al. ........ 606/200 |
| 5,180,368 A * | 1/1993 | Garrison ..................... 604/104 |
| 5,192,286 A | 3/1993 | Phan et al. |
| 5,308,354 A | 5/1994 | Zacca et al. |
| 5,330,484 A | 7/1994 | Günther et al. |
| 5,354,295 A | 10/1994 | Guglielmi et al. |
| 5,395,311 A | 3/1995 | Andrews |
| 5,411,509 A | 5/1995 | Hilal |
| 5,423,829 A | 6/1995 | Pham et al. |
| 5,449,372 A | 9/1995 | Schmaltz et al. |
| 5,454,795 A | 10/1995 | Samson |
| 5,456,667 A | 10/1995 | Ham et al. |
| 5,490,859 A | 2/1996 | Mische et al. |
| 5,527,326 A | 6/1996 | Hermann et al. |
| 5,628,761 A | 5/1997 | Rizik |
| 5,643,297 A | 7/1997 | Nordgren et al. |
| 5,643,298 A | 7/1997 | Nordgren et al. |
| 5,695,469 A | 12/1997 | Segal |
| 5,728,123 A | 3/1998 | Lemelson et al. |
| 5,728,129 A | 3/1998 | Summers |
| 5,769,871 A | 6/1998 | Kelly et al. |
| 5,779,722 A | 7/1998 | Shturman et al. |
| 5,792,157 A | 8/1998 | Mische et al. |
| 5,795,322 A | 8/1998 | Boudewijn |
| 5,827,324 A * | 10/1998 | Cassell et al. ............... 606/200 |
| 5,833,644 A | 11/1998 | Zadno-Azizi et al. |
| 5,836,868 A * | 11/1998 | Ressemann et al. ........ 606/159 |
| 5,843,103 A | 12/1998 | Wulfman |
| 5,855,565 A * | 1/1999 | Bar-Cohen et al. ......... 604/104 |
| 5,895,398 A | 4/1999 | Wensel et al. |
| 5,972,019 A * | 10/1999 | Engelson et al. ............ 606/200 |
| 6,096,053 A * | 8/2000 | Bates ......................... 606/159 |

* cited by examiner

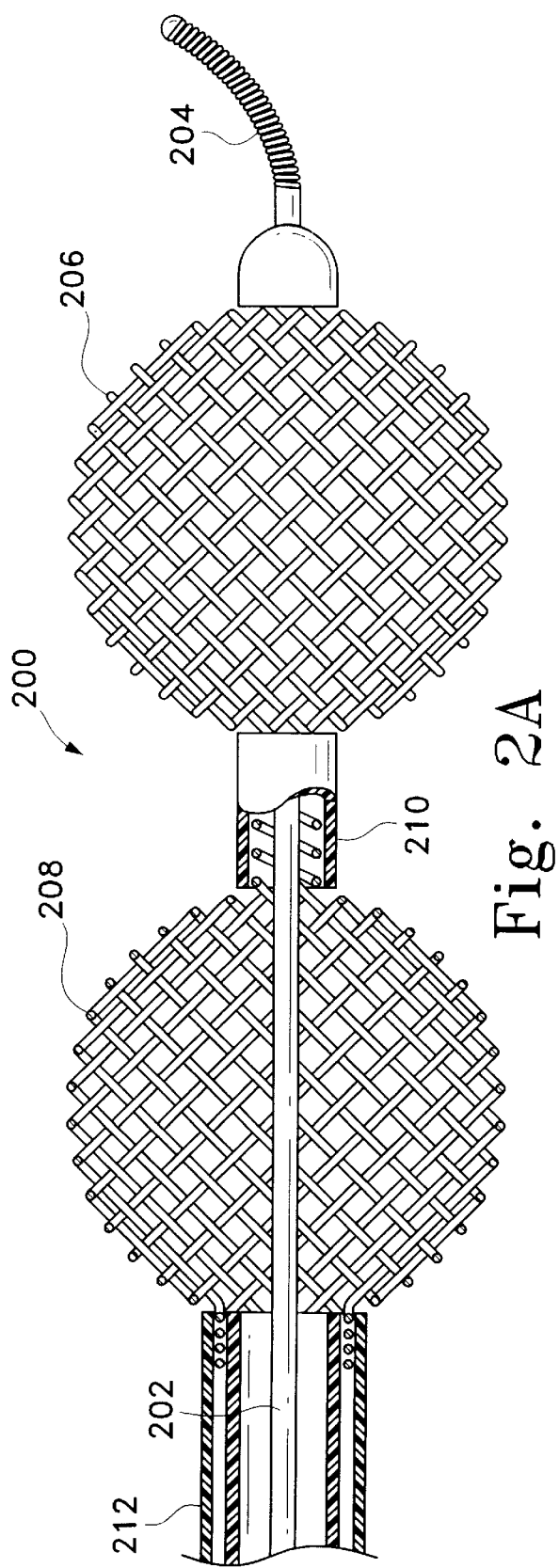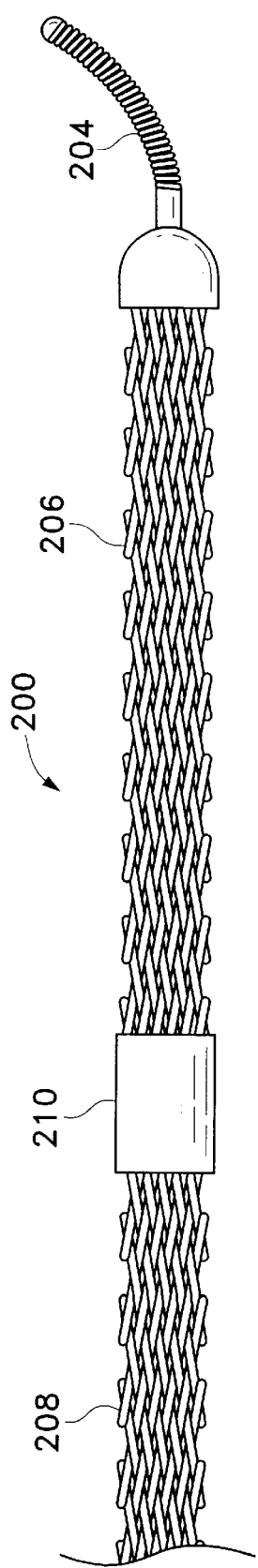
Fig. 2A
Fig. 2B

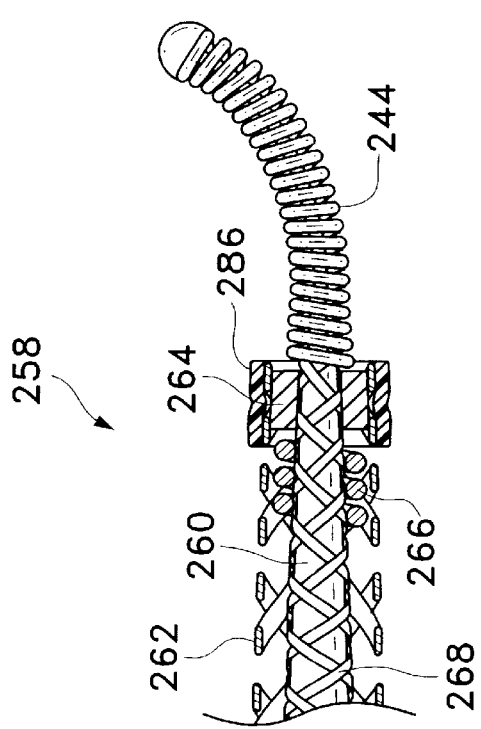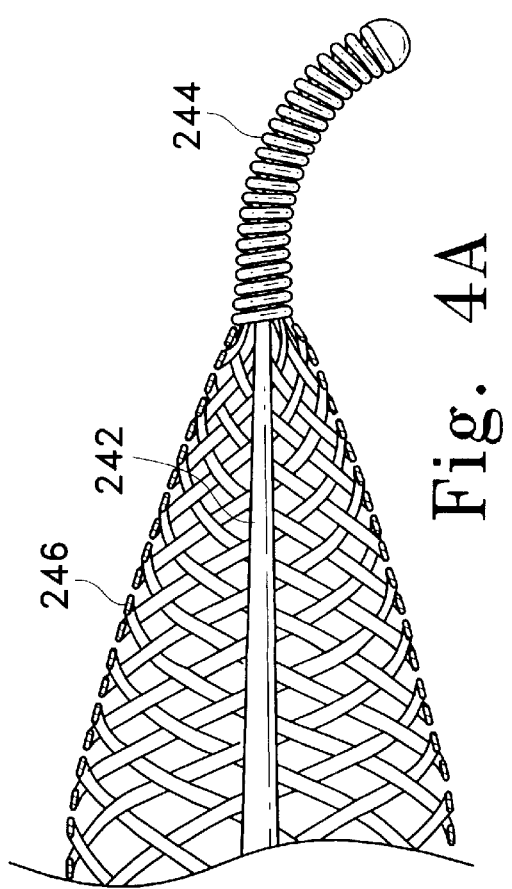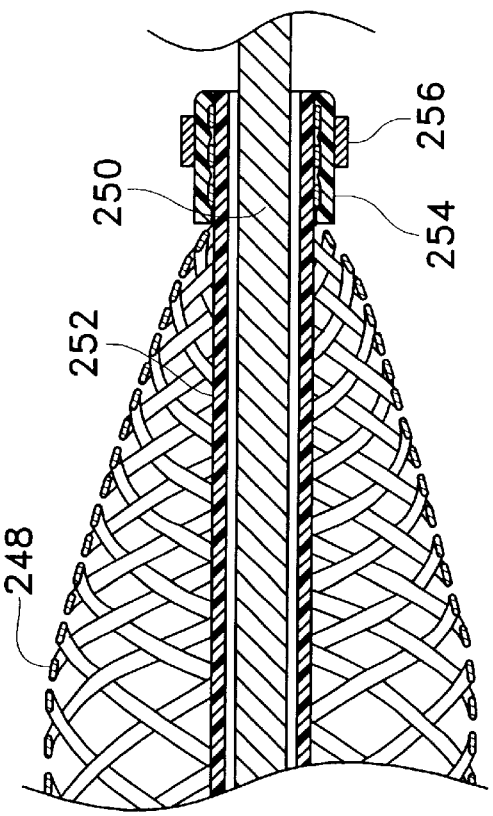

MECHANICAL CLOT TREATMENT DEVICE WITH DISTAL FILTER

CROSS REFERENCE TO RELATED PATENT APPLICATION

This application is a continuation of U.S. patent application Ser. No. 08/941,514, filed Sep. 30, 1997, now U.S. Pat. No. 6,066,149, the entirety of which is hereby incorporated by reference.

FIELD OF THE INVENTION

This is a medical device used to treat embolic strokes. In particular, it is a surgical device usually delivered through an intravascular catheter. It may be used in several ways. It may, for instance, be used to open a clear passageway adjacent a thrombus to allow both blood and medication to bypass the clot. It may be used to pierce and to remove a thrombus. These thrombi are often found in tortuous vasculature. The device may include several sections: an elongated core element, a proximal cage assembly, a distal filter, and an actuator. The core element is at least a core wire. Placed around the distal end of the core element is a collapsible, but preferably self-expanding or self-collapsing, proximal cage assembly and a more distally located, preferably self-expanding or self-collapsing, distal filter, cage assembly, or other filter component. These components are preferably radio-opaque. The proximal end of the proximal cage is typically is affixed to an actuator in such a way as to allow expansion of the cage after deployment. The proximal cage assembly may be used for collecting emboli or for displacing them to allow blood flow to resume, either with or without concurrent clot-dissolving drug treatment. The distal sector, whether a cage or a fan, is placed distally of the thrombus to collect portions of the thrombus which may loosen during the treatment or removal procedure.

BACKGROUND OF THE INVENTION

This surgical device is designed to displace or to penetrate emboli found in the human vasculature. The device has several major components including a proximal (or displacing cage) and a distal filter. Depending upon the chosen procedure, the device is inserted so that the displacing or proximal cage is either towards the venous side of the clot or adjacent the clot. The proximal cage is expanded either to displace the clot away from the arterial wall and allow flow of fluid (e.g., blood and medications such as anti-thrombolytics or other lysing agents) past (or to) the formerly occluded site or to engage the clot for removal using the cage as a collector assembly, expand once past the target emboli, and catch or net the embolism (or a portion of embolism) for removal from patient's blood vessles. In some situations, the device may be used to move the clot to another position in the vasculature; perhaps for recovery using another device or to canalize the clot for improved blood flow. The distal filter member is always placed distal to the thrombus to catch any portions which may break away.

Other devices to treat vascular emboli are known. The use of inflatable balloons to remove emboli has been practiced for many years. The "Fogarty catheter" has been used, typically in the periphery, to remove clots from arteries found in legs and in arms. These well known devices have been described in some detail in U.S. Pat. No. 3,435,826, to Fogarty and in U.S. Pat. Nos. 4,403,612 and 3,367,101. These patents describe a balloon catheter in which a balloon material is longitudinally stretched when deflated.

Emboli occasionally form around the valves of the heart and then are dislodged and follow the blood flow into the distal regions of the body. They are particularly dangerous if the emboli passes to the brain and causes an embolic stroke. As will be discussed below, many such occlusions lodge in the middle cerebral artery (MCA), although such is not the only site where emboli come to rest. Obviously, when blood flow is inhibited or cut off completely from a portion of the brain, the brain's oxygen supply is limited causing severe health problems.

In procedures for removing emboli using the Fogarty catheter or other similar catheters, it is typical, first, to locate the clot using fluoroscopy. The embolectomy catheter is then inserted and directed to the clot. The distal tip of the balloon catheter is then carefully moved through the center of the clot. Once the balloon has passed through the distal side of the clot, the balloon is inflated. The balloon catheter is then gradually and gently withdrawn. The balloon, in this way, acts to pull the clot ahead of the balloon. The majority of procedures using a Fogarty catheter repeat these steps until the pertinent vessel is cleared of clot material.

Such vaso-occlusions occur in a wide variety of sites within the body. The lodging of thrombus in various sites is often complicated by the presence of atherosclerosis. This disease causes the vessels to become tortuous and narrowed. These anomalies are often considered to be the result of the growth of atherosclerotic plaque. Clots occurring in these diseased vessels are difficult to remove using balloon or Fogarty catheters.

Removal of emboli using balloon catheters is rife with potential problems. One such problem occurs during removal of a clot. The resistance to such removal often causes the balloon portion of the catheter to evert over the tip of the catheter. Should the user need to partially deflate the balloon during such a deflation, the distal tip of the balloon may become distended and angulate. Another difficulty with balloon catheters is the possibility of damage to the intima of arteries. Inflation pressures can create forces significant enough to score such a vessel lining or dislodge plaque lodged on such a wall. In the worst case, the balloon may rupture leaving balloon portions in the bloodstream.

Movement of a balloon in the MCA using only a balloon can displace the clot through more proximal branches into other large vessels such as the internal carotid artery (ICA) and then into other vessels and may pressure the clot into branching vessels.

There are a variety of different devices intended for use in replacing balloon catheters and in using a device other than a balloon catheter in so removing the emboli.

One such device is shown in U.S. Pat. No. 4,030,503 to Clark III. This patent describes a spiral helix affixed to the distal end of a catheter. In particular, the spiral helix is designed to be rotated and pushed forward through the clot. It is said that the helix screws into the clot, and when it is firmly embedded or is past the clot, the catheter is pulled out of the vessel without rotation. The catheter is said to operate like a corkscrew.

A similar catheter is described in U.S. Pat. No. 4,706,671 to Weinrib. This catheter also has a coil section at its distal end. The coil section is said to be stretched initially into a generally linear insertion position for removing inwardly in a vessel. The coil member is then expanded into the form of a hollow conical scoop to then scoop clot material from the blood vessel. The coil member is stiffened by an internal wire which is then removed. The hollow passageway is then filled with a liquid to stiffen the coils. The coils are said to be of an elastomeric material.

U.S. No. Pat. 4,762,130 to Fogarty et al., describes a helical balloon attached to the distal end of a catheter. The helical or bellowed balloon is maintained in a generally linear condition and passed into a clot. Once the catheter balloon within the clot is inflated, the balloon and adjoining clot are removed together.

Another similar device used more to grip and shear atherosclerotic deposits rather than to remove thrombi is described in U.S. Pat. No. 4,890,611 to Monfort et al. This device incorporates a pair of helical wires placed on the distal end of a wire. The flexible wire is pulled against a flexible catheter and the two helically configured loops expand to form a shearing apparatus. The totality of the apparatus is then twisted by means of a handle so that the pair of helically wound loops cuts through and is said to retain sections of plaque for removal from the vessel.

Another thrombus extraction system is shown in U.S. Pat. No. 5,011,488, to Ginsberg. In using this device, an inflatable balloon having a proximal conic shape is deflated and passed through a thrombus. It is then expanded and retracted so that the proximal passage pulls the thrombus into contact with an aspirator. The aspirator then removes the clot or thrombotic material from the vessel.

An alternative configuration of the expandable member is also described in the Ginsberg patent mentioned just above. In this variation, a wire coil is attached to an extension wire which may be moved between an extended position and a retracted position. The retracted or expanded configuration is illustrated to have a conical shape. The cone is shown to be one which has a smaller end proximally.

U.S. Pat. No. 5,112,347, to Taheri, shows an inflatable balloon type embolectomy catheter. The balloon has a number of fingers arranged in a leaf spring arrangement inside the balloon. The balloon is hydraulically inflated and forms a cone after inflation. The deflated device is shown in FIGS. 11 through 14 to be passed distally past an embolism before inflation. After inflation, the large end of the balloon collects the embolism as it is pulled past the appropriate site in the vessel.

U.S. Pat. No. 5,192,286, to Phan, shows a retrieval catheter for removing materials from various body lumen. The retrieval catheter is shown to have a slack net which may be collapsed for passage into a lumen past the material to be collected. The net is unfolded and materials such as uretral stones are removed.

U.S. Pat. No. 5,411,509 to Hilal, shows an embolectomy catheter having an elastomeric foam tip attached distally. The foam tip has an actuator means suitable for forming the foam section both longitudinally and radially in response to activation of the actuation means. In practice, the catheter tip is pressed past an embolism, inflated, and retracted with the clot being pushed proximally as retraction occurs.

U.S. Pat. No. 5,490,859, to Mische et al., shows an intravascular occlusion material removal device having an expandable material removal element made up of a number of wires passing between the two ends of such element, a catheter shaft, a drive shaft for spinning the material movement element within the blood vessel, and a collection portion placed on the material removal element for collecting any occlusion material removed by the expandable material removal element. The drive shaft may be operated by a motor connected to the proximal end of the drive shaft.

None of these devices show the device described below.

SUMMARY OF THE INVENTION

This is a surgical device usually delivered through an intravascular catheter. It is designed variously to displace or to pierce and remove emboli particularly when found in tortuous vasculature.

This embolectomy device includes several sections. First, the device has a core element. The core element preferably has at least several major functions: first, the distal portion may act as a guidewire for vessel navigation to the treatment site; second, the distal portion assists in puncturing the clot or displacing it away from the arterial wall; and third, it cooperates with the collection assembly during the deployment of that assembly. The core element may be a simple core wire (perhaps enhanced with an adherent braid) fixedly attached to the distal end of the cage assembly or a tubular member attached to the collection assembly having a removable core or guidewire in its interior passageway. Preferably, the core element is able to rotate freely with respect to collection assembly to preserve its abilities as a guidewire while preserving the cage assembly shape and integrity.

Placed distally on the core element are a pair of cage or filter elements. The proximal element preferably is an expandable and collapsible self expanding cage assembly. The proximal element may be self-expanding or self-collapsing. The distal element may also be a cage and design similar to the proximal element or of other filter design. The distal element is intended to catch any errant thrombus or clot fragments. Both elements may either be fixedly or rotatably joined to the core wire. Most preferred of the designs for the cage assembly involves a super-elastic alloy ribbon or wire braid wrapped with a platinum wire or otherwise made radio-opaque.

The assembly further may have an actuator which permits or causes the assembly to expand or to contract after deployment. The actuator may be mechanical in nature or electrolytic, or may include a balloon. When the actuator is mechanical, it is typically attached to the proximal end of the proximal cage assembly to allow or cause controllable expansion of the distal and proximal cage assemblies.

BRIEF DESCRIPTION OF THE DRAWINGS

FIGS. 2A and 2B show a side, partial cutaway and a side view of the distal end of one variation of the device respectively as expanded and as unexpanded.

FIGS. 4A, 4B, and 4C show, respectively, side views of various distal tips of the device.

DESCRIPTION OF THE INVENTION

This device is a surgical implement. It is designed variously to move a thrombus aside and provide a fluid passageway along that thrombus or to penetrate and at least partially to retrieve emboli situated in human vasculature. It is intended to be used rapidly as a flow restoration device. Even in those instances where the embolism is not or cannot be completely removed, this inventive device is believed to be useful in displacing, extracting, or removing a portion of the clot and thereby permitting restoration of partial blood flow. It can be used to move the clot to a more advantageous site in the body. It is suitably flexible to be placed in the distal tortuous vasculature of the brain and hence is useful in treating blocking emboli found there. This device may be considered a partial treatment for embolic stroke, for instance, when used with the addition of thrombolytics.

Figure 1:
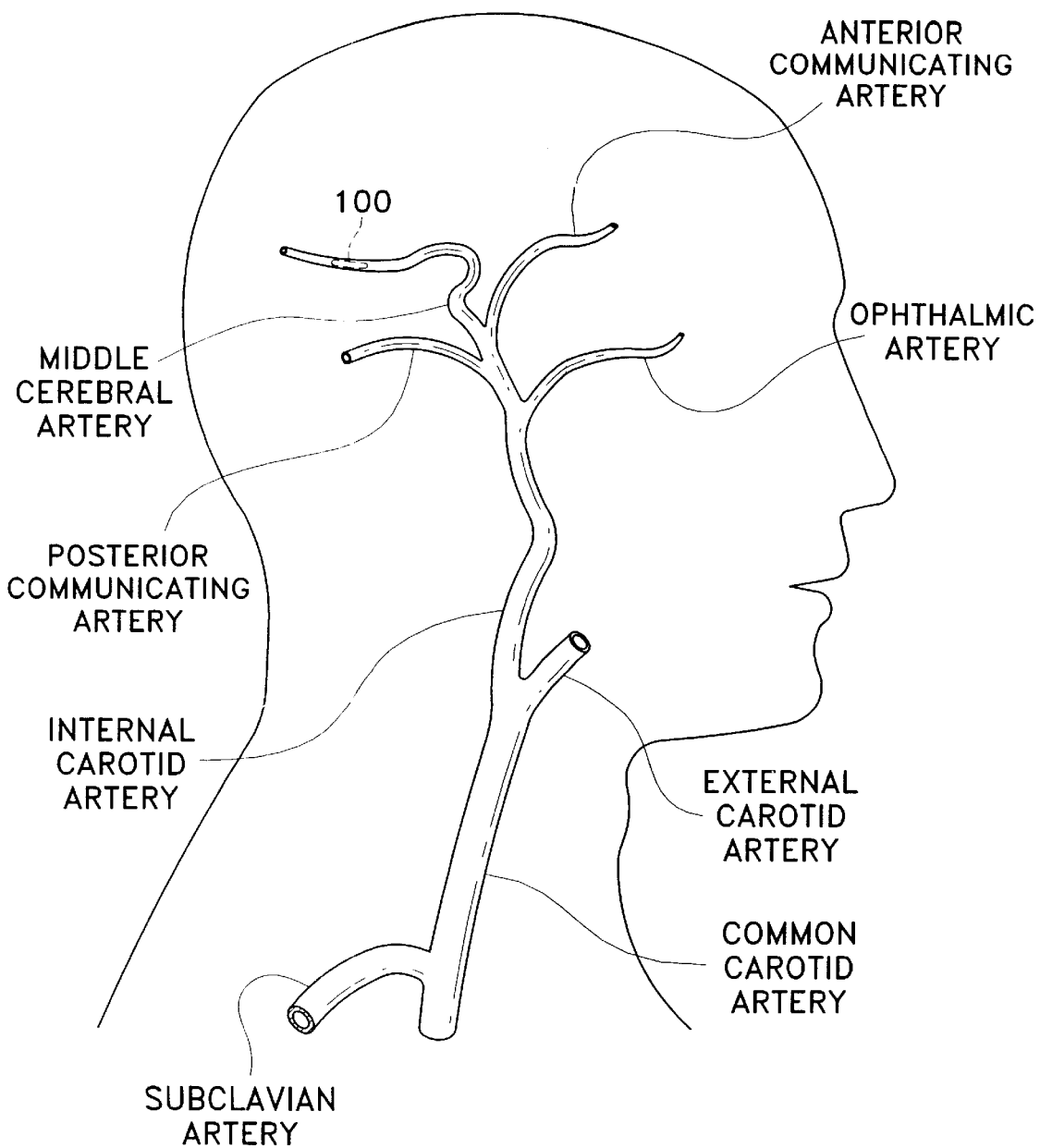
FIG. 1 shows a generalized schematic of a portion of the arterial system of the head specifying in particular the position of an embolism in the middle cerebral artery.

As a matter of practical experience, a large proportion of emboli sloughed into the brain are seldom longer than about 1 to 2 centimeters and, for a variety of reasons both physiological and hemodynamic, settle in the middle cerebral artery (MCA). As is shown in FIG. 1, the path from the site of origin of a traveling embolus—often the heart—to the MCA is via the common carotid artery past the branch point forming the external and internal carotid arteries into the internal carotid artery (ICA). The MCA is generally considered to be the continuation and termination of the ICA after the siphon and after the branching sites of a variety of other arteries, e.g., the ophthalmic artery, the anterior communicating artery, the posterior communicating artery, and others. The etiology of such an occlusion is varied, varying, and complicated. The occlusion (100) is shown in the MCA in FIG. 1 at the noted site.

Treatments for such embolic occlusions include catheterization of the patient and introduction of tissue plasminogen activator (TPA) or urokinase or other clot lysing agents to the site of the occlusion. Additionally the embolic occlusion may be penetrated—often with a microcatheter—and the TPA or urokinase introduced distally of the occlusion. Removal of the catheter provides a modest passageway for resumed or increased blood flow past the then-partial occlusion.

This inventive device is for the rapid restoration of fluid or blood flow past the occlusion. We have found that it may be used in a variety of ways. For instance, when approaching the clot from the arterial end, the device can be used either to bypass the clot along the vessel wall and, upon expansion of the proximal cage assembly, to allow flow of blood across the occlusion using the interior of the proximal cage assembly as a fluid passageway.

Alternatively, the inventive device may be used to canalize or remove an occlusion, via the steps of penetrating the occlusion, expanding a cage assembly distally of the embolism, and preferably removing at least a part of the embolism along with the cage and its attendant catheter.

The distal cage or filter element is to catch and retain any thrombus fragments and prevent them from moving distally.

FIG. 2A is a diagrammatic portrayal of the major portions of a desired variation (200) of the device and provides a general convention for several of the terms used herein.

The assembly typically includes a core element, often a core wire (202), and optional coil tip (204) to provide a measure of radio-opacity to the distal tip and protect against damage to the intima, a distal cage assembly, filter, or element (206) which may be used as an embolism collector, and a proximal cage assembly or element (208). Because of the "fineness" of the device, the coil tip (204) may also serve the same function as a guidewire tip. The length of the coil tip (204) may be up to 4 or 5 centimeters in such instances. Further, and as is discussed below, the core element may be an assembly comprising a tubular member further containing a removable core or guidewire. In one highly desirable variation of the invention, a separation member (210) is used to separate distal cage or element (206) from the proximal cage (208). As will be explained in greater detail below, a preferred variation of the invention is one in which the distal member (206) and the proximal cage (208) are made of a single tubular member woven variously from wire or ribbon. The two cages are separated by a separation member (210) which, as seen in partial cross section in FIG. 2A, is a simple tubular member made from, e.g., an appropriate metal or polymer.

The distal cage assembly (206) and proximal cage assembly (208) are collapsible for passage along-side of or for penetration and passage through the embolism and are generally self expandable once in position. Other components and devices may, obviously, be used to expand the distal cage assembly (206) and proximal cage assembly (208), are discussed at some length below.

The distal cage assembly (206) and proximal cage assembly may either self-expand when the actuator element (212) is permitted to move from its introduction position to its deployment position or it may self-collapse. Self-collapsing may provide a measure of safety in the event that the device becomes inoperable. Withdrawal of a collapsed device is simpler than is removal of an expanded device. The actuator element (212) is operable by the person.

FIG. 2B shows the shape of the variation shown in FIG. 2B in the form in which it is introduced. Actuator (212) (not shown) has been pulled proximally against the core wire (202) (not shown in FIG. 2B). As will be shown below, this slim or first configuration passes through an appropriately sized delivery catheter and may be pushed by or through a clot prior to expansion to the deployed or second configuration shown in FIG. 2A.

The distal cage assembly (206) and proximal cage assembly (208) are preferably made of a super-elastic alloy wire or ribbon. Some stainless steels are suitable but the ready availability of nickel-titanium alloys in a wide variety of shapes and sizes makes this choice an easy one. In particular, we have found that ribbons as thin as 0.75 mils in thickness and as narrow as 2 mils in width are suitable for this device. Thicker and wider ribbons are also suitable in some instances as the situation requires. Preferred ribbons are between 0.75 and 1.5 mils in thickness and 3 and 7 mils in width. Most preferred are 0.8 mils and 4 mils respectively.

By "wires" we mean to include filamentary shapes having cross-sections where the thickness/width ratio is greater than 0.5 to and including 1.0. The cross-sectional form may be circular, square, oval, etc.

At least a minority of the ribbons may be a suitable stainless steel (e.g., 304SS, 306SS, etc.) or other such alloy. A desirable variant is the substitution of one or more ribbons of the braid (or the addition of one or more ribbons) with a radio opaque material such as platinum. This obviously permits the user to visualize the position of the distal cage assembly (206) and proximal cage assembly (208) during a procedure.

A technical basis for the term "super-elastic" is found in the class of nickel titanium alloys known as "nitinol"— alloys discovered by the United States Naval Ordnance Laboratory. These materials are discussed at length in U.S. Pat . No. 3,174,851 to Buehler et al., U.S. Pat. No. 3,351,463 to Rozner et al., and U.S. Pat. No. 3,753,700 to Harrison et al. Alloys especially suitable for this invention are those containing at least 1.5% (wt.) and up to about 8% (wt.) or more, of one or more alloying members selected from the group consisting of vanadium, chromium, manganese, iron, and cobalt. By the term "ribbon", we intend to include elongated shapes, the cross section of which are not square or round and may typically be rectangular, oval, or semi-oval. They should have an aspect ratio of 0.5 (thickness/width) or less.

The distal cage (206) and proximal cage (208) may be made by winding a ribbon or a wire onto a mandrel having an exterior form to produce the relaxed shape found in FIG. 2A. The mandrel and wound ribbon are preferably heated for a suitable period of time (e.g., 750° to 1200° F. for one-half to two hours) to produce an assembly which has the portrayed shape. For use in the MCA, the outer diameter of the device after deployment need not be any larger than about 3 mm. It is desirable that the collapsed or non-deployed device have a diameter no larger than about 1 mm. The expansion ratio between any of the deployed and deployable devices discussed herein typically need not be any more than about 3:1 to be effective in the MCA. Expansion ratios between 2:1 and 10:1 are appropriate in this invention. These ratios are suitable for each variation of the invention. The invention is not so limited, however.

In some designs of the device, it is permissible to use an actuator as an active deployment element rather than as a mere restraint on the premature expansion of the cage assembly. Examples of such actuators are shown in U.S. patent application Ser. Nos. 08/686,304, 08/701,155, and 08/869,346 assigned to Target Therapeutics and all of which are incorporated by reference.

Figure 3A:
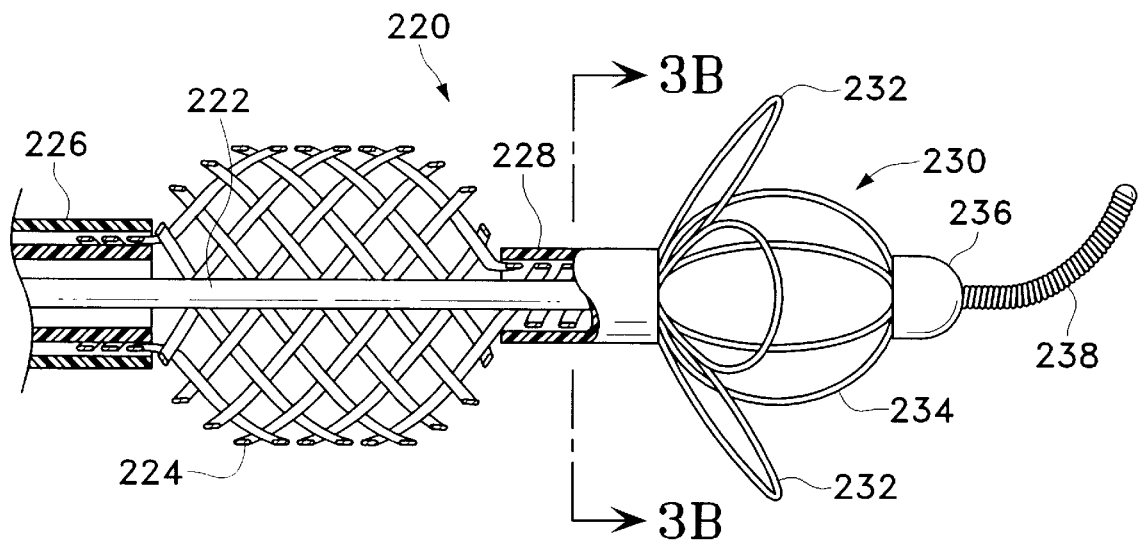
FIGS. 3A and 3B show, respectively, a side, partial cutaway and an end view of another variation of the device.
Figure 3B:
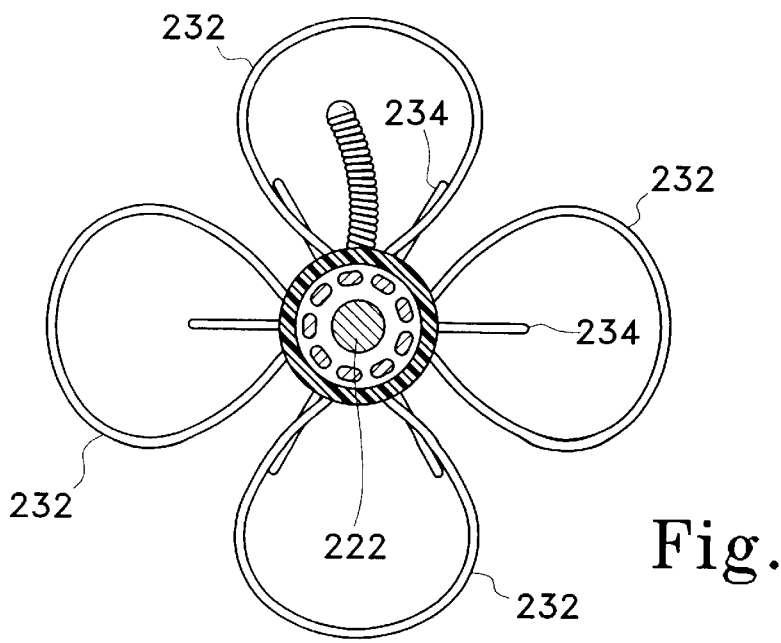

FIGS. 3A and 3B show a cross-section of another variation of the inventive device related to that variation found in FIGS. 3A and 3B but employing a slightly more complicated distal cage or filter assembly.

FIGS. 3A and 3B show respectively a partial cross-section of a further variation (220) of the invention shown, as above, a device having a central core wire (222) and a proximal cage assembly (224). Proximal cage assembly (224) is shown to be a woven braid of ribbons, preferably of a superelastic alloy, but as with variations in this Application, may be made of wires as that term is defined herein. It is to be seen from FIG. 3A that the shape of the proximal cage assembly (224) is somewhat more columnar than that shown in FIG. 2A. This shape is a preferred one because of its ease of manufacture. It may be produced in such a way that it is of significant length for use in long emboli. Actuator tubular member (226) is also shown in this variation, as is separator element (228). A major difference from the variation (200) shown in FIGS. 2A and 2B is the structure of the distal filter assembly (230). Although the structure of distal filter assembly (230) is not critical to the concepts of this invention in that it may be of any desirable shape capable of catching small bits of emboli sloughed from the embolus against which a proximal cage assembly (224) is pressing, the depicted distal filter assembly (230) is exempletive of the shape of assemblies suitable for placement on this section of the overall assembly. In this variation, a plurality of petal-shaped wires (232) which may or may not overlap when deployed, are seen. Optional spacer wires (234) are seen as supporting assembly tip member (236) to provide the distal end of core wire (238) with a measure of radial placement.

FIGS. 3A and 3B show the distal assembly in its deployed configuration.

Because of the distal rake of filter members (232), those filter members (232) may be easily retracted into a catheter lumen when one desires to remove this device from the human body.

FIGS. 4A, 4B, and 4C show various distal treatments of the overall device. As has been noted above, the core wire may be fixed within the cage members, it may be provided with limited movement axially within the cage members, or it may be provided with full axial movement in which case the core wire acts and may be used as a guidewire for the device.

FIG. 4A shows a very simple variation of the invention in which a core wire (242) is fixably attached to a distal coil (244). The distal coil (244) also serves as an anchoring means for the distal cage assembly (246). This variation of the invention is simple and inexpensive and is suitably useful particularly when the device need not be extended too far into tortuous vasculature.

FIG. 4B shows another variation of the invention also having a woven braided ribbon distal cage (248). However, unlike the variation shown in FIG. 4A, this variation utilizes a core wire (250) which is freely moveable axially through the center of that distal cage (248). The distal cage (248) has a tubular liner (252) which moves independently of the actuator (shown in FIGS. 2A and 3A above). Core wire (250) does act as a guidewire and may be used to provide a pathway through tortuous vasculature for the device to follow. Liner (252) is preferably made of a material such as polytetrafluoroethylene (e.g., Teflon) and desirably extends all the way to the proximal end of the catheter and acts as an actuator for the cages. A desirable variation of this invention includes the securing of distal cage assembly (248) by use of a tubular member of, e.g., a thermoplastic, which fixes the distal-most end of distal cage assembly (248) to inner liner (252). A radio-opaque marker (256) (which is optional in this variation for reasons which will be explained below) is also depicted.

FIG. 4C shows a further variation (258) of this invention in which core wire (260) is rotatable with respect to distal cage (262) but has limited axial movement therein. This obviously allows the user to position the bent coil tip (244) in a position to select or sub-select from turns or Y's in the tortuous vasculature without twisting the whole device (258). Limitation of the movement of the core wire (260) within the device (258) is accomplished via the use of bushing (264) placed distally in the distal cage assembly (262). The inner diameter of bushing (264) will not allow coil (244) to pass proximally nor will it allow coil (266) to pass distally. Coil (266) may be used as a marker coil if so desired. Bushing (264) also desirably forms a joint with outer tubular member (286) to firmly place the distal-most end of distal cage assembly (262).

An independent feature shown in FIG. 4C is the presence of a braid member (268) which is adherent to core wire (260). Braid member (268) is for the specific purpose of providing kink resistance and improved torqueability. The material used as a braid on the core wire (260) may be any of a different number of materials. Highly desirable, though, is the use of a braid of super-elastic alloy. Certain classes of these materials have been discussed in detail above. The braid material (268) may be stainless steel wire or polymeric filament. In some variations, materials known as Liquid Crystal Polymers (LCP's) may be employed simply because they have extremely high tensile strength and do not easily stretch. This braid allows the overall diameter of the core wire assembly—the core wire (260) and the braid (268)—to be smaller than a core wire having appreciably the same performance. These more complex designs may be useful in situations in which extremely small vasculature must be penetrated to treat the errant thrombus.

Figure 5A:
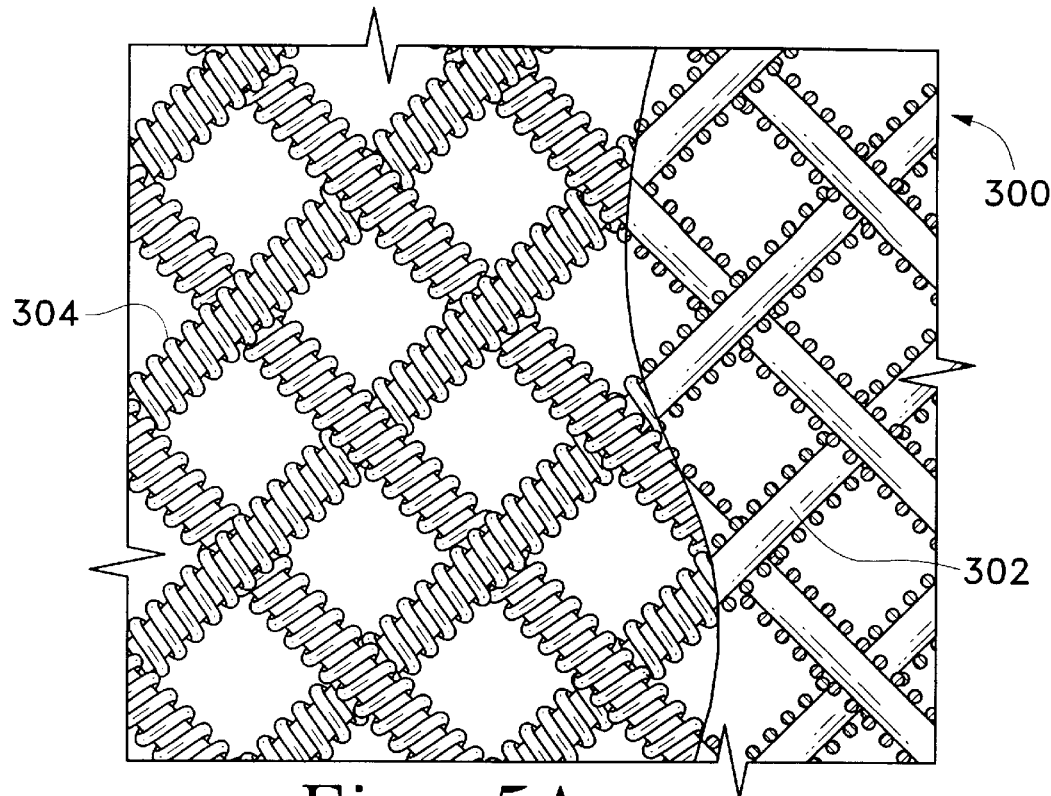
FIG. 5A shows a close-up of braid section comprised of a wrapped wire.
Figure 5B:
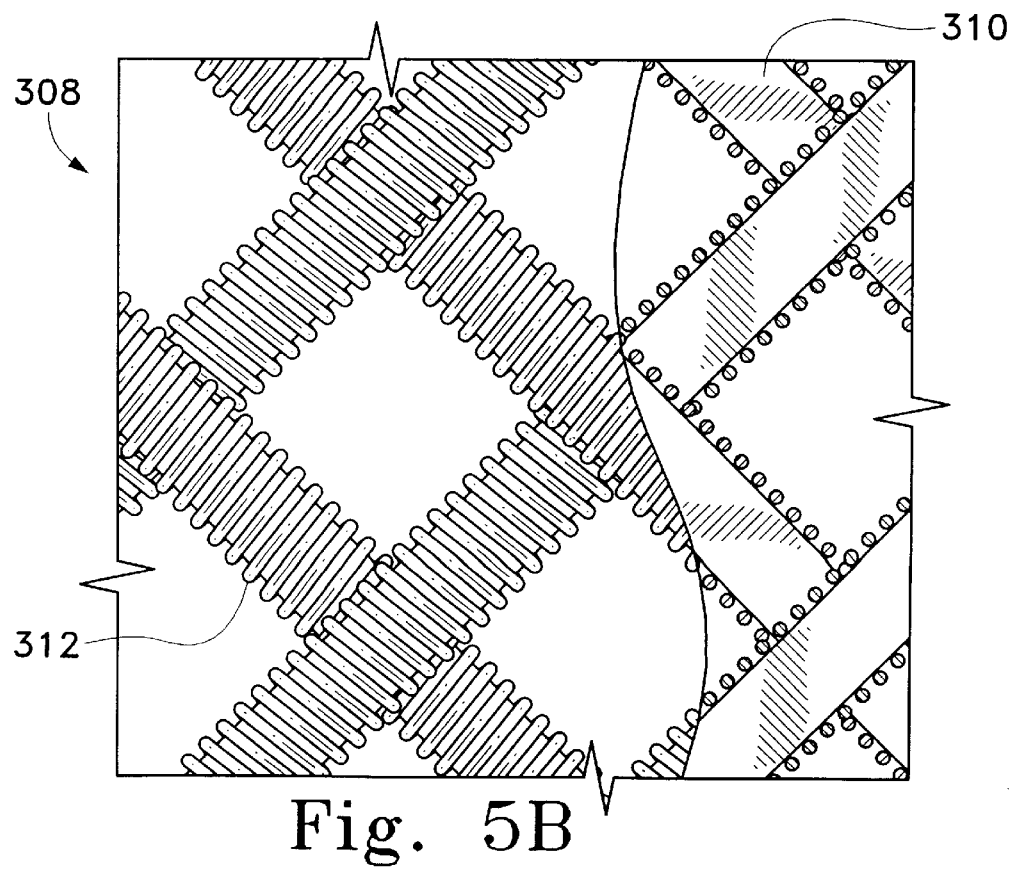
FIG. 5B shows a close-up of braid section comprised of a wrapped ribbon.

As noted elsewhere, the location of the cage assembly should be visible using fluoroscopy. Various methods have been suggested above. One highly preferred method is shown in FIGS. 5A and 5B. In essence, at least some of the elements (ribbons or wires) making up the cage assemblies are provided with significant radio-visibility via the placement of a radio-opaque covering on these elements. A metallic coating of a metal having comparatively more visibility, during fluoroscopic use, than stainless steel is preferred. Such metals are well-known but include gold and members of the Platinum Group of the Periodic Table, e.g., platinum, palladium, rhenium, rhodium, etc. The cage assembly wires or ribbons may be electroplated or otherwise provided with a continuous coating but a thick coating may be had by wrapping the element with a radio-opaque wire or ribbon.

Another material suitable for such a service is a structural material filled with a radio-opaque material. For instance, a suitably fine tubing of, e.g., nitinol or stainless steel, filled with platinum or gold is commercially available. Fort Wayne Metals of Fort Wayne, Indiana sells such a product as a "drawn filled tube."

FIG. 5A shows a portion of a cage assembly (300) made up of a woven braid of wires (302) which in turn are tightly wrapped with radio-opaque wires (304). The right side of FIG. 5A is a partial cut away showing the wires (302) and the radio-opaque wires (304) in cross-section.

As an example of the device shown in FIG. 5A, we have found that nickel/titanium super-elastic alloy wire having a diameter in the range of 0.001 to 0.004wrapped with 0.0001 to 0.002diameter platinum wire is suitable and is quite visible.

FIG. 5B shows a partial cut-away of a cage assembly (308) constructed of ribbon (310) as described above and further wrapped with radio-opaque wires (312). As was the case with the FIG. 5A variation, the right side of the drawing is a partial cut away showing the internal ribbon (310).

The variations of the cage assemblies shown in FIGS. 5A and 5B may be used in place of any of the cage assemblies found elsewhere herein.

Figure 6A:
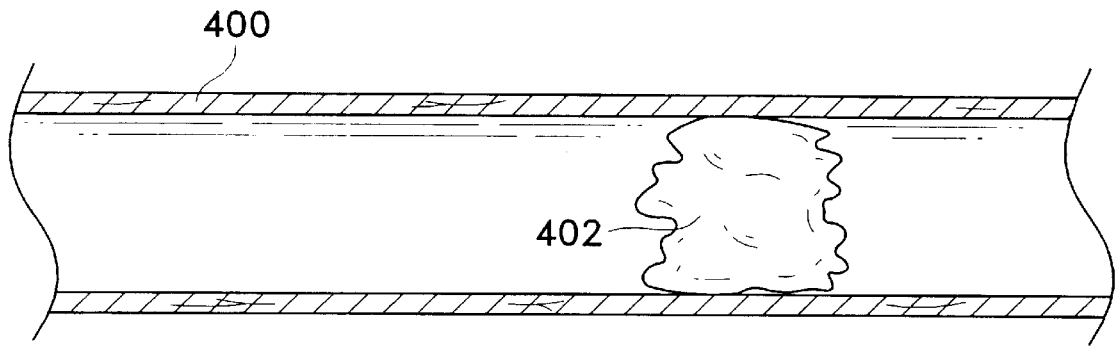
FIGS. 6A, 6B, 6C, and 6D show a generalized sequence of steps for use of the inventive device for displacing a thrombus for restoration of flow past the occluded site.
Figure 6B:
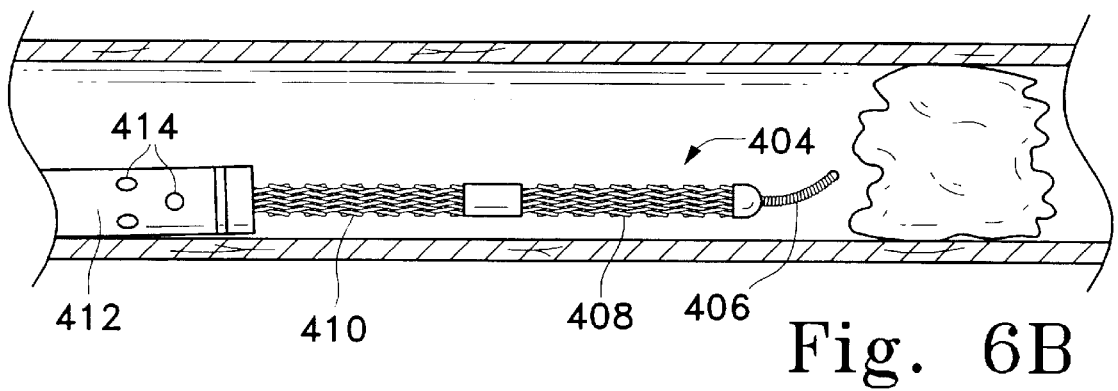

FIGS. 6A to 6D, show in generic fashion, one method of using the device described herein FIG. 6A schematically depicts an artery (400) containing a blocking clot (402). Blood flow through artery (400) is severely compromised. A variation of the inventive device (404) similar to that shown in FIGS. 2A and 2B is shown in the artery (400) in FIG. 6B. This variation (404) has a rotatable core wire (406) which is useful as a guidewire. It has a distal woven braided cage assembly (408), a proximal braided cage assembly (410) and a tubular actuator (420). Also shown is the delivery catheter (412) having orifices (414) for perfusion of appropriate medicines.

Many clots such as clot (402) will push the core wire (406) tip aside as the guidewire contacts the clot. Indeed, in most instances, such is preferred. The core wire (406) then slips along the wall of the artery (400) as the device (404) is advanced.

Figure 6C:
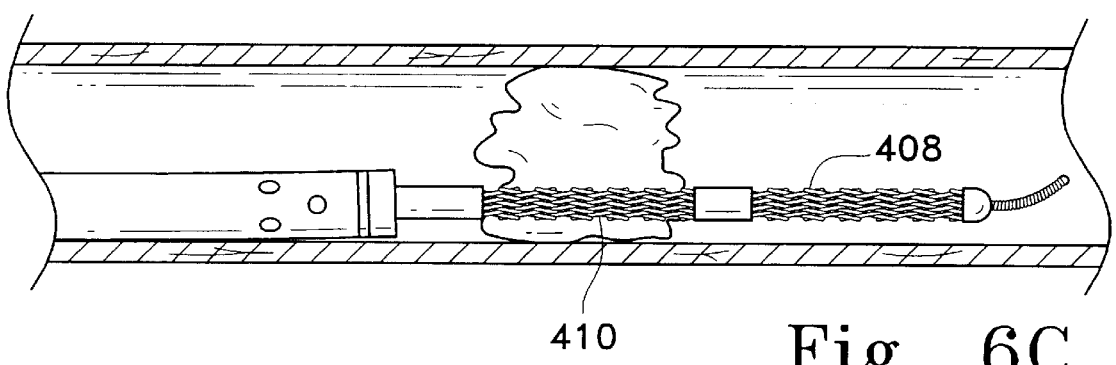
Figure 6D:
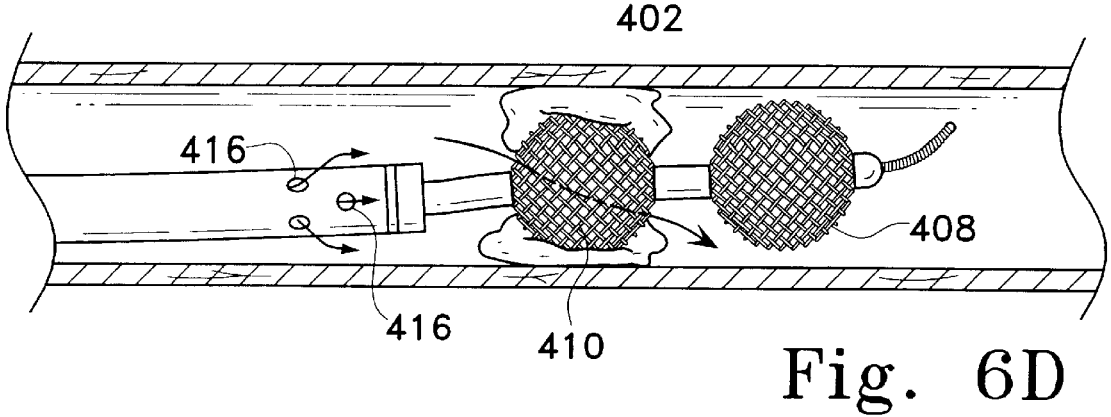

FIG. 6C shows an appropriate placement of the distal cage assembly (408) past the occlusion (402) and of the proximal cage assembly (410) adjacent to the clot prior to deployment. The proximal cage assembly (410) length assembly is desirably selected so that it overlaps both ends of clot (402).

Upon expansion of the cage assemblies (408, 410) to their expanded shape, blood will flow from the arterial to venous end of the clot (402) through the lumen of the open proximal cage assembly (410). Desirably, distal cage assembly (408) has an expanded diameter which approximates the size of the artery (400) lumen. The distal filter assembly (408) is there solely to prevent distal movement of the clot (402) or fragments of the clot. Thrombolytics may be introduced through the orifices (416) to dissolve clot (402). It is highly desirable that the proximal cage assembly (410) be used to restrain the clot (402) from movement in the vessel (400) so that the thrombolytics may completely dissolve the clot (402) while so restrained. This procedure obviously provides a continuing source of thrombolytics to the clot (402) and further provides a large clot surface area upon which the thrombolytics may work.

Alternatively, or in addition to the steps outlined above, clot (402) can be retained or retrieved by the expanded distal cage assembly (408) and removed to another site along with the distal cage assembly (408) and catheter (412).

It should be apparent that the cage assembly of this invention may be recollapsed and re-deployed as necessary to displace or collect emboli as necessary or desired.

The design of such variations is routine and is within the skill of an ordinary designer in this art. Similarly, obvious variants of the invention described above are within the scope of the invention. This and other known or non-critical items have been omitted from the drawings for the sake of brevity and clarity of the invention disclosed here.

We claim as our invention:

1. A removable flow restoration device comprising:
    a core element having a distal portion for navigation to a therapeutic site in a lumen and for assisting in puncturing or displacing an occlusion,
    a first filter comprising braided ribbons distally located on the core element for collecting, displacing, or moving the occlusion,
    a second filter comprising braided ribbons located on the core element distal to the first filter for placement distal to the occlusion to catch the occlusion or fragments thereof,
    a separation member which separates the first filter from the second filter,
    wherein the core element passes through the first and second filters,
    an actuator for expanding or collapsing the first filter and second filter about the core element, and a flexible tip located on a distalmost end of the core element.

2. The removable flow restoration device of claim 1 wherein the actuator is electrolytically activated.

3. The removable flow restoration device of claim 1 wherein the actuator is mechanically activated.

4. The removable flow restoration device of claim 1 wherein a ratio of an outer diameter of the first filter when expanded to an outer diameter of the first filter means when collapsed is between about 2 to 1 and 10 to 1.

5. The removable flow restoration device of claim 1 wherein a ratio of an outer diameter of the second filter when expanded to an outer diameter of the second filter when collapsed is between about 2 to 1 and 10 to 1.

6. The removable flow restoration device of claim 1 wherein the core element is axially moveable within the first and second filter means.

7. The removable flow restoration device of claim 1 wherein the core element is rotatable with respect to and non-removable from the first filter means.

8. A removable flow restoration device comprising:
    a core element comprising at least an elongated core wire having a distal end and a proximal end,
    a proximal cage located substantially coaxial about the core element through which the core element passes,
    a separator element located substantially coaxial about the core element and distal to a proximal cage,
    a distal cage located distal to the separator element, the distal cage comprising a plurality of petal-shaped members, at least one of which has a distal rake, the core element passing through at least the first cage, a tubular actuator for expanding and contracting at least the proximal cage, located substantially coaxial about the core element and proximal to the proximal cage, and a coil tip member located distal to the distal cage.

9. The removable flow restoration device of claim 8 wherein the proximal cage comprises a woven braid of ribbons.

10. The removable flow restoration device of claim 8 wherein at least a portion of the proximal cage comprises a superelastic alloy.

11. The removable flow restoration device of claim 8 wherein at least a portion of the petal-shaped members comprises wires.

12. The removable flow restoration device of claim 8 wherein at least a portion of the first cage or second cage is radio-opaque.

13. The removable flow restoration device of claim 8 wherein the core element passes only through the first cage.

14. The removable flow restoration device of claim 8 wherein the distal cargo self-expanding.

15. An embolism treatment device comprising:

a core element comprising at least an elongated core wire having a distal end and a proximal end, a proximal cage located substantially coaxial about the core element through which the core element is axially movable, a woven braided distal cage located substantially coaxial about the core element and distal to the proximal cage, through which the core element is axially movable within a tubular liner, and an actuator for expanding and contracting the proximal and distal cages, located substantially coaxial about the core element and proximal to the proximal cage, and a flexible core wire tip located on a distalmost end of the core element means.

16. The embolism treatment device of claim 15 wherein the tubular liner is polymeric.

17. The embolism treatment device of claim 16 wherein the tubular liner comprises polytetrafluoroethylene.

18. The embolism treatment device of claim 15 additionally comprising a tubular member located substantially coaxial to the core element and distal to the distal cage for affixing a distal end of the distal cage to the tubular liner.

19. The embolism treatment device of claim 18 additionally comprising a radio-opaque marker affixed to the tubular member.

20. The embolism treatment device of claim 15 wherein a ratio of an outer diameter of the proximal cage when expanded to an outer diameter of the proximal cage when collapsed is between about 2 to 1 and 10 to 1.

21. The embolism treatment device of claim 15 wherein a ratio of an outer diameter of the distal cage when expanded to an outer diameter of the distal cage when collapsed is between about 2 to 1 and 10 to 1.

* * * * *

UNITED STATES PATENT AND TRADEMARK OFFICE
CERTIFICATE OF CORRECTION

PATENT NO.    : 6,383,205 B1  Page 1 of 1
DATED         : May 7, 2002
INVENTOR(S)   : Gene Samson and Harold F. Carrison It is certified that error appears in the above-identified patent and that said Letters Patent is hereby corrected as shown below:

<u>Column 7,</u>
Lines 56-60, replace "configuration.
Because of the distal rake of filter members (232), those filter members (232) may be easily retracted into a catheter lumen when one desires to remove this device from the human body." with
-- configuration. Because of the distal rake of filter members (232), those filter members (232) may be easily retracted into a catheter lumen when one desires to remove this device from the human body."

<u>Column 9,</u>
Line 35, replace "herein" with -- herein. --

Signed and Sealed this

Eighth Day of June, 2004

JON W. DUDAS
*Acting Director of the United States Patent and Trademark Office*